US012800580B2

(12) United States Patent
Sarhan et al.

(10) Patent No.: US 12,800,580 B2
(45) Date of Patent: Nov. 17, 2026

(54) ELECTRIC, MAGNETIC, AND RF SENSOR BASED METHODS TO REGISTER AND INTERPRET LATERAL FLOW ASSAY MEASUREMENTS

(71) Applicant: Xtrava, Inc., Santa Clara, CA (US)

(72) Inventors: Sameh Sarhan, Santa Clara, CA (US); Lawrence H. Zuckerman, Santa Clara, CA (US)

(73) Assignee: Xtrava, Inc., Santa Clara, CA (US)

( * ) Notice: Subject to any disclaimer, the term of this patent is extended or adjusted under 35 U.S.C. 154(b) by 1046 days.

(21) Appl. No.: 18/053,052

(22) Filed: Nov. 7, 2022

(65) Prior Publication Data

US 2023/0067165 A1 Mar. 2, 2023

Related U.S. Application Data

(62) Division of application No. 16/121,476, filed on Sep. 4, 2018, now Pat. No. 11,493,511.
(Continued)

(51) Int. Cl.
*G01N 33/543* (2006.01)
*G01D 5/14* (2006.01)
(Continued)

(52) U.S. Cl.
CPC ....... *G01N 33/54388* (2021.08); *G01D 5/145* (2013.01); *G01R 29/14* (2013.01);
(Continued)

(58) Field of Classification Search
CPC .... G01N 33/558; G01N 27/127; G01N 27/22; G01N 27/227; G01N 27/228;
(Continued)

(56) References Cited

U.S. PATENT DOCUMENTS

2006/0281193 A1 12/2006 Petrilla et al.
2010/0261286 A1 10/2010 Kim et al.
(Continued)

FOREIGN PATENT DOCUMENTS

WO 2013083686 A1 6/2013

OTHER PUBLICATIONS

Cesar Fernandez-Sanchez, et al. Disposable Noncompetitive Immunosensor for Free and Total Prostate-Specific Antigen Based on Capacitance Measurement. Analytical Chemistry, vol. 76, No. 19, eight pages, Oct. 1, 2004.
(Continued)

*Primary Examiner* — Christopher L Chin
(74) *Attorney, Agent, or Firm* — AVEK IP, LLC

(57) ABSTRACT

A method for reading a lateral flow assay test strip comprises providing a microwave antenna in proximity of a stain line region of the test strip. The method includes causing a chemical compound to travel to the stain line region, an amount of the chemical compound varying in accordance with a quantity of an analyte. The method comprises connecting an instrumentation to the microwave antenna. The method includes measuring a feed impedance of the microwave antenna using the instrumentation, the feed impedance of the microwave antenna varying with the amount of the chemical compound. The method comprises determining the quantity of the analyte based on the feed impedance of the microwave antenna.

11 Claims, 8 Drawing Sheets

Related U.S. Application Data

(60) Provisional application No. 62/555,368, filed on Sep. 7, 2017.

(51) Int. Cl.
*G01R 29/14* (2006.01)
*G01R 33/09* (2006.01)
*G01R 33/12* (2006.01)

(52) U.S. Cl.
CPC ....... *G01R 33/091* (2013.01); *G01R 33/1269* (2013.01); *G01R 33/1276* (2013.01)

(58) Field of Classification Search
CPC ......... G01N 33/54346; G01N 33/5438; G01N 33/54387; G01N 33/54388; G01N 2035/00108; G01N 2291/018; G01D 5/145; G01R 29/14; G01R 33/091; G01R 33/1269; G01R 33/1276; G01R 27/26; B01L 2300/0645; B01L 2300/0825
USPC ..... 73/862.337, 862.627; 422/401, 420, 425, 422/82.01, 82.02; 435/287.2, 287.7, 435/287.9, 805, 970; 436/514, 525, 530, 436/806
See application file for complete search history.

(56) References Cited

U.S. PATENT DOCUMENTS

| | | | |
|---|---|---|---|
| 2014/0323350 | A1 | 10/2014 | Nguyen et al. |
| 2017/0067889 | A1 | 3/2017 | Tamir |

OTHER PUBLICATIONS

Jacqueline M. Barnett, An Inexpensive, Fast and Sensitive Quantitative Lateral Flow Magneto-Immunoassay for Total Prostate Specific Antigen, Biosensors, 2014, 204-220, 4; doi: 10.3390/bios4030204.

James Frake, et al. Radio-frequency capacitance spectroscopy of metallic nanoparticles. Scientific Reports, Jun. 4, 2015, six pages, 10858; doi: 10.1038/srep10858 (2015).

P. Georgia Chris Selwyna, Development of Electrochemical Biosensor for Breast Cancer Detection Using Gold Nanoparticle Doped CA 15-3 Antibody and Antigen Interaction, 2013 International Conference on Signal Processing, Image Processing and Pattern Recognition [ICSIPRI, seven pages, PSG College of Technology, Coimbatore, India. (2013).

ELECTRIC, MAGNETIC, AND RF SENSOR BASED METHODS TO REGISTER AND INTERPRET LATERAL FLOW ASSAY MEASUREMENTS

CROSS REFERENCE TO RELATED APPLICATIONS

The application is a divisional of U.S. patent application Ser. No. 16/121,476, filed Sep. 4, 2018, Now U.S. Pat. No. 11,493,511 and titled "Electric, Magnetic, And RF Sensor Based Methods to Register and Interpret Lateral Flow Assay Measurements," which claims priority to U.S. Provisional Patent Application Ser. No. 62/555,368, filed Sep. 7, 2017 and having the same title. Priority is claimed to each of these applications and the disclosure of each is hereby incorporated by reference in its entirety.

FIELD OF THE DISCLOSURE

This disclosure relates generally to instruments that determine the presence and/or quantity of chemical compounds. More specifically, this disclosure relates to automated instruments that use the lateral flow technique.

BACKGROUND

For at least 50 years, the lateral flow assay method has been known for its ability to provide handy determination of the presence and amounts of various substances. Before 1960, in a related method called electrophoresis, samples containing a mixture of proteins were deposited on absorbent paper strips and later to gel media. An electric field or potential was applied to the medium, causing proteins of various charge values to migrate at different speeds, thus separating them as a fractionation procedure. Perhaps, the most famous applications for the lateral flow assay method are pregnancy tests, but the method is used for thousands of compounds and in at least hundreds of industries.

The principal value of said lateral flow assay method is low cost, portability, and ease of use, including by those who are unskilled with analytical chemistry. A liquid sample, that may or may not contain a target chemical compound, "analyte" is applied to one end of a test strip consisting of absorbent material that draws said sample by capillary action the entire length thereof, wetting said strip as it goes.

If and only if said sample contains said target analyte, chemical means keyed to the target compound at two locations along the strip cause a "stain" line to be formed at a certain position thereon, as the remains of the liquid sample passes to the far end, assisting with capillary action.

If a stain line is identified by the user, the analyte is considered as present within the liquid sample. However, owing to low concentration and/or other factors, the stain line can be indistinct, causing the determination to be difficult and/or unreliable, especially for the non-expert user. Even expert users can have difficulty, and it may be critical for the particular test to be definitive. Even worse than discarding a test, it may be interpreted incorrectly. Therefore, professional laboratories sometimes use expensive video image analysis equipment on the "noisy" stain.

The purpose of the invention described in the instant disclosure is to achieve the superior analysis capabilities of expensive optical analysis equipment using a readout method and apparatus that could eliminate the need for visual inspection and be so inexpensive that consumers could easily own them for home use. The positive impact on society of such widespread use capability should not be underestimated. Witness the revolution in diabetes care that resulted from accurate home testing of blood glucose levels.

SUMMARY

The following presents a simplified summary of the invention in order to provide a basic understanding of some aspects of the invention. This summary is not an extensive overview of the invention. It is not intended to identify critical elements of the invention or to delineate the scope of the invention. Its sole purpose is to present some concepts of the invention in a simplified form as a prelude to the more detailed description that is presented elsewhere herein.

Returning to the long-existing Lateral Flow Assay method, a liquid sample, that may or may not contain a target chemical compound, "analyte" is applied to one end of a test strip consisting of absorbent material that draws said sample by capillary action the entire length thereof, wetting said strip as it goes. There are two major positions along the strip. At the first position is a pre-deposited chemical means that changes its chemical composition only if the analyte is present. The pre-deposited chemical means is carried with the sample fluid to the second major position whether or not the keyed analyte is present—whether or not its composition is changed. At the second major position is pre-deposited an additional chemical means. If the first chemical means is in an unchanged composition state, it is not attracted to the second chemical means and passes to the far end of the strip. If the first chemical means is in a changed composition state, it is attracted to the second chemical means and collects at the second major position, building up a stain line that is visible upon inspection as a positive test for the presence of the analyte.

Instead of requiring visual inspection, which may be unreliable, the method taught in the instant disclosure measures the concentration of pre-deposited chemical means using electric and/or magnetic probe sensors pre-installed to the test strip along with each chemical means. Another type of sensor, utilizing RF/microwave probes, could be present only in a test fixture. These sensors could measure changes in total dielectric constant or permeability in the immediate vicinity of their locations, especially at the second major position where concentration of pre-deposited chemical means collects when analyte is present. Moreover, as a quantitative electrical signal having a large dynamic range resulting from the sensors, a concentration level of analyte could be estimated, instead of only presence or absence. It should be understood that the visual stain line inspection method possesses a small dynamic range, even when augmented with optical analysis equipment. Finally, as a means to gather additional information, electronic sensors and instrumentation are capable of dynamic measurements during the wicking process instead of a single measurement when wicking is complete.

In an embodiment, a method for reading a lateral flow assay test strip comprises providing a microwave antenna in immediate proximity of a stain line region of the test strip. The method includes causing a chemical compound to travel to the stain line region. An amount of the chemical compound varies in accordance with a quantity of an analyte. The method comprises connecting an instrumentation to the microwave antenna, the instrumentation including a radio frequency meter. The method comprises measuring a feed impedance of the microwave antenna using the instrumentation, the feed impedance of the microwave antenna varying with the amount of the chemical compound. The method includes using the variation in the feed impedance of the microwave antenna to determine the quantity of the analyte.

In another embodiment, a method for reading a lateral flow assay test strip comprises providing a microwave antenna in proximity of a stain line region of the test strip. The method includes causing a chemical compound to travel to the stain line region, an amount of the chemical compound varying in accordance with a quantity of an analyte. The method comprises connecting an instrumentation to the microwave antenna. The method includes measuring a feed impedance of the microwave antenna using the instrumentation, the feed impedance of the microwave antenna varying with the amount of the chemical compound. The method comprises determining the quantity of the analyte based on the feed impedance of the microwave antenna.

In yet another embodiment, a method for reading a lateral flow assay test strip comprises providing a microwave antenna in proximity of a stain line region of the test strip. The method includes causing a chemical compound to travel to the stain line region, an amount of the chemical compound varying in accordance with a quantity of an analyte. The method comprises connecting an instrumentation to the microwave antenna. The method includes measuring a feed impedance of the microwave antenna using the instrumentation, the feed impedance of the microwave antenna varying with the amount of the chemical compound. The method includes determining the quantity of the analyte based on the feed impedance of the microwave antenna using a test fixture.

Other aspects, features and advantages of the invention will be apparent to those skilled in the art from the following Disclosure.

BRIEF DESCRIPTION OF THE SEVERAL VIEWS OF THE DRAWINGS

Illustrative embodiments of the present disclosure are described in detail below with reference to the attached drawing figures and wherein.

DETAILED DESCRIPTION

The various figures, and the various embodiments used to describe the principles of the present invention in this patent document are by way of illustration only and should not be construed in any way to limit the scope of the invention. Those skilled in the art will understand that the principles of the invention may be implemented in any type of suitably arranged device or system.

In general, this disclosure provides a non-optical, wide dynamic range sensor and electronic method to assess the results of lateral flow assay measurements.

Depending on the implementation, this technique can provide significant benefits in a range of fields, such as chemical analysis for medical and industrial applications.

Figure 1:
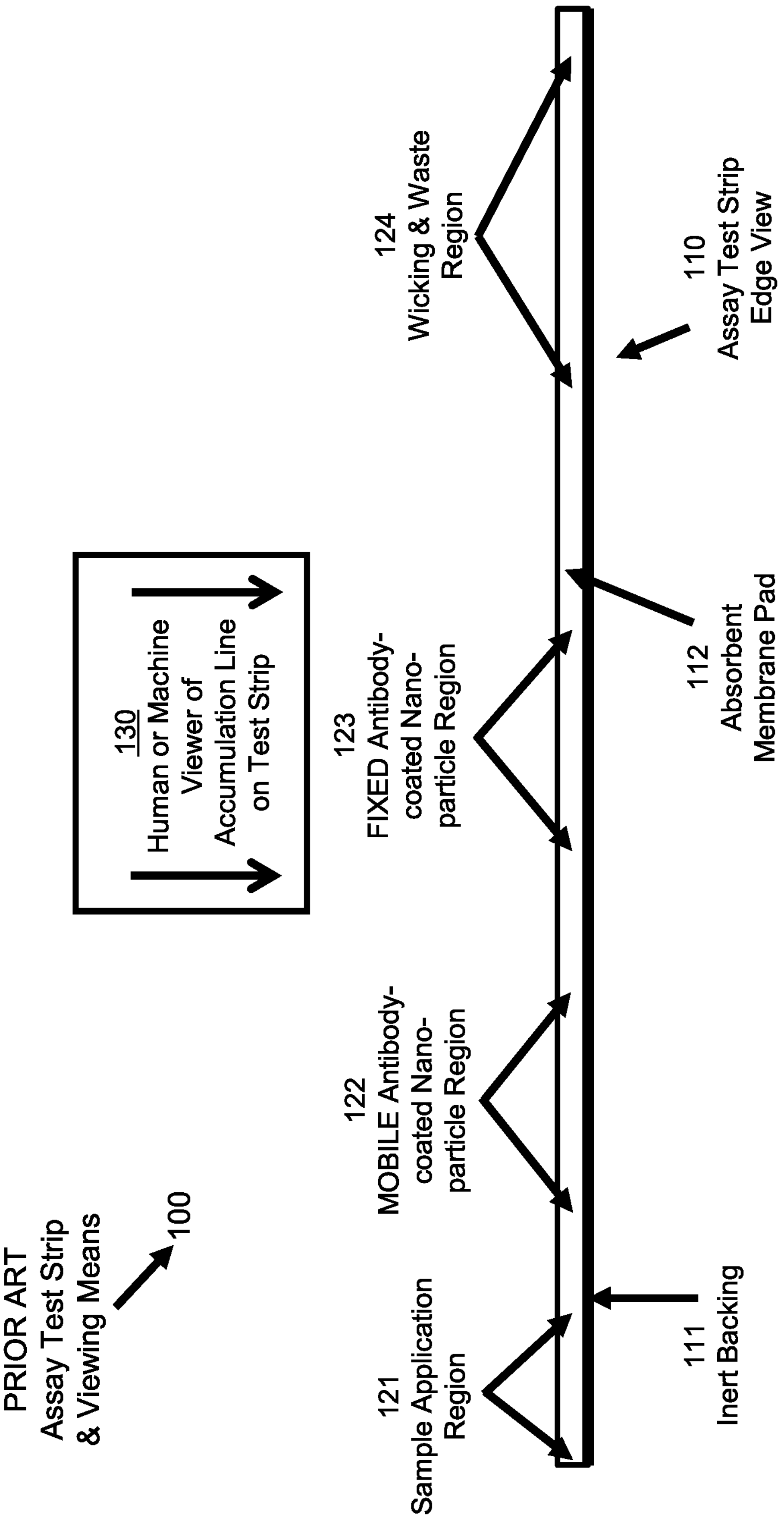
FIG. 1 illustrates an example prior art Lateral Flow Assay test strip system used to determine the presence or absence of a chosen substance.

FIG. 1 illustrates an example prior art Lateral Flow Assay test strip system 100 used to determine the presence or absence of a chosen substance, also known as the analyte, within a liquid. Said test strip consists of a chemically inert backing 111 that may also provide physical strength and stability, and an attached absorbent membrane 112, whose function is to transport liquids from Sample Application Region 121 to Wicking and Waste Region 124, after passing through Regions 122 and 123 described below.

Located in Region 122 is a deposition of non-reactive metallic or non-metallic nanoparticles that are coated with an antibody substance that is specifically chosen to conjugate with the analyte. These nanoparticles are not permanently attached to the absorbent membrane and will therefore be carried by the fluid sample as it travels along the membrane. Clustered near the center of Region 123 is a deposition of identical coated nanoparticles, but in this case, they are permanently attached to the absorbent membrane and will not travel with the sample fluid. The region to the right of Region 123, especially Region 124, is used to as an extension of the strip to help draw the sample fluid through Region 123 via capillary action and to provide a storage location for the sample fluid and waste products.

If the sample fluid applied at Region 121 does not include the Analyte, when it reaches Region 122, the antibody substance is unchanged as the nanoparticles travel with the sample fluid to Region 123. When they arrive at Region 123, they do not react with or attach to the nanoparticles there and continue to travel with the sample fluid to Region 124.

If the sample fluid applied at Region 121 contains the Analyte that corresponds with the antibody substance coating the nanoparticles present at Regions 122 and 123, there is a different scenario. When the sample fluid reaches Region 122, it carries the nanoparticles toward Region 123 as in the previous case, but at Region 122 and during the travel to Region 123, the Analyte, according to its concentration, reacts ("conjugates") with the antibody substance on some fraction of the nanoparticles.

The product of this reaction bears an affinity for the antibody substance on all remaining nanoparticles that have not reacted with the Analyte. Conjugated antibodies, (still coating nanoparticles) have an additional property when attached to nanoparticles with un-conjugated antibodies—they change color, allowing visual knowledge of the conjugation and attachment.

When the nanoparticles reach Region 123, remaining conjugated but unattached coated nanoparticles attach themselves to the immobile unconjugated coated nanoparticle there. These nanoparticles are therefore trapped in Region 123 and accumulate, creating a visible line that indicates presence of the Subject Analyte in the sample fluid. This visible line can be viewed by Human or machine/instrumented viewing means 130.

Figure 2:
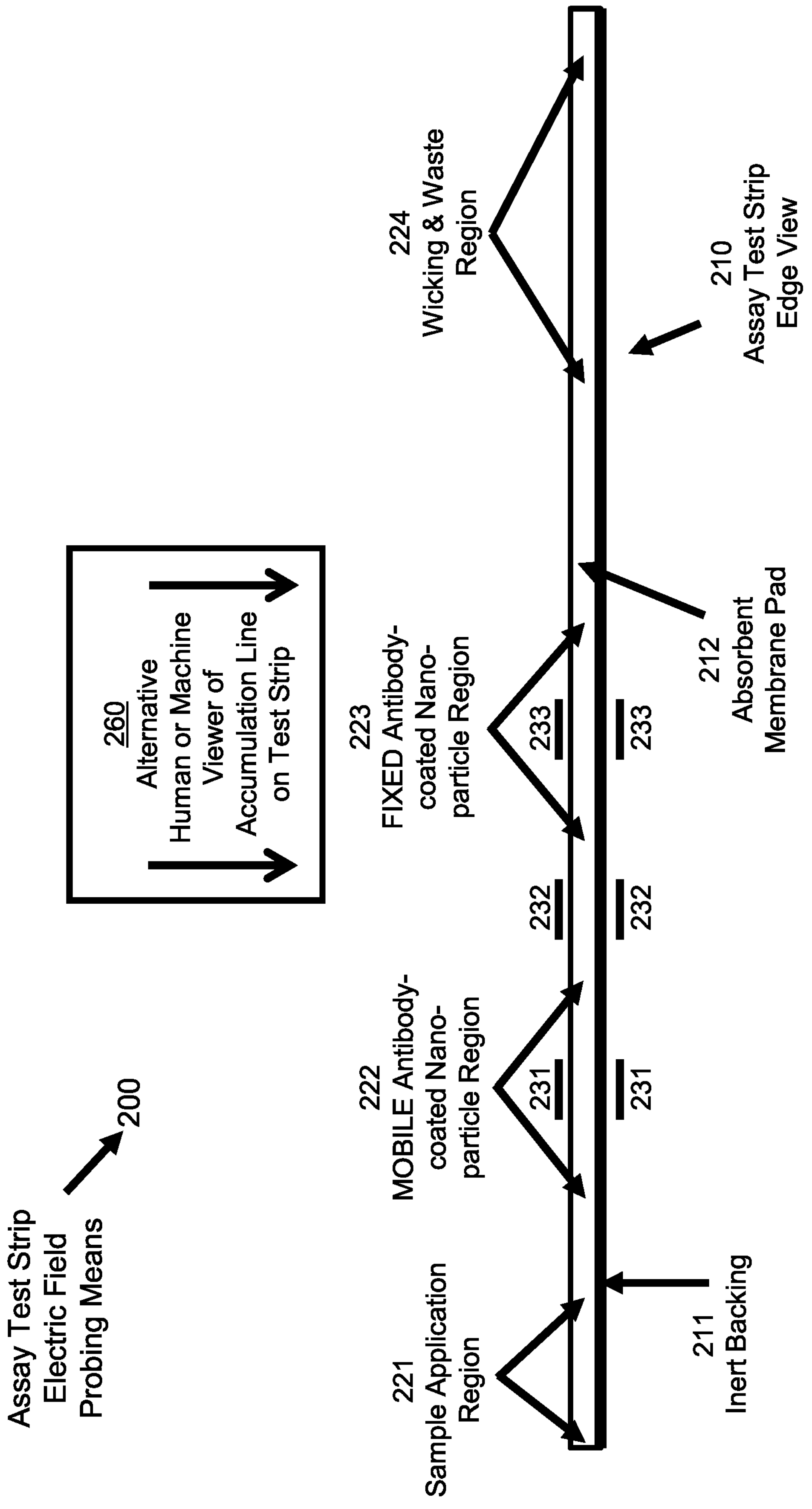
FIG. 2 illustrates an example method to employ the same lateral flow assay test method but register the result without need for manual or automated optical inspection.

FIG. 2, a novel approach, illustrates an example method to employ the same lateral flow assay test method but register the result without need for manual or automated optical inspection. Moreover, quantitative measurement of the Analyte will be facilitated.

FIG. 2 shows a series of electric field sensors 231, 232, 233 added to the test strip assembly. Not shown in the figure are necessary wiring to connect the sensors and all necessary electronic circuitry. In order to conserve the cost of said assay test strip, which is used only for a single test, the amount of electronic circuitry present on it is minimized. Direct electrical connection to the test strip can be used, but the need for such means and any on-board power source can also be eliminated through the use of wireless "RFID tag" methods and other wireless means.

Each electric field sensor 231, 232, and 233 consists of parallel planar electrodes, shown edge-on in FIG. 2. Each of the planar electrode sets 231, 232 and 233 could be connected to an AC or DC circuit that causes an electric field that permeates the test strip membrane in its immediate vicinity. For an AC excitation circuit, the electrode set 231, 232, and 233 presents a reactance that is a function of frequency. Depending upon the average dielectric constant between the electrodes, i.e. the dielectric constant integrated over all volume elements, the reactance at a given frequency will vary. As the number of nanoparticles increases, the average dielectric constant increases, decreasing the reactance. As the electrodes are situated closer to the strip, the average dielectric constant is a stronger function of the number of nanoparticles.

As is well known in the field of electronics, there are numerous types of circuitry that respond to the average dielectric constant of whatever is between or in the immediate vicinity of said electrodes. For example, the electrodes could be connected to an oscillator circuit, whose frequency will change in accordance with the average dielectric constant. As the number of nanoparticles increases, the frequency will drop. Electrodes 231, 232, 233 could be connected to circuitry located on the test strip, or within a test fixture, not shown. The test strip could be mated with the test fixture either immediately after the sample has been applied, for effects to be recorded as a function of time, or at any time after the wicking process has ceased.

The principal region to measure average dielectric constant, using electrode set 233, is Region 223; as this is where the nanoparticles congregate and remain permanently if the analyte, which matches the antibody, is present in the liquid sample.

Following the test, when all flow has ceased, average dielectric constant readings at Region 222 and between Regions 222 and 223 assist with calibration and measurement sensitivity, accuracy, and reliability. Such readings could also be made prior to the test, either just prior, or at manufacture, and recorded on the assembly, including electronically.

In order to avoid raising the cost of assay test strip 210 by adding electrodes 231, 232, 233, these electrodes could be attached to a test fixture (not shown), which would also contain the remaining circuitry needed to measure the average dielectric constant at the various test strip Regions. When inserting the test strip into the test fixture, it would be guided to cause each of its various Regions to be situated between the corresponding set of electrodes.

Summarizing the various configurations: 1) The sensors and all primary measuring circuitry could be located on the test strip. 2) The sensors could be located on the test strip, with all primary measuring circuitry located on the test fixture. 3) The test strip could have no additional elements, with the sensors and all primary measuring circuitry located on the test fixture.

Block 260 represents the same human or apparatus viewer/analyzer of the nanoparticle concentration line at location 223 as shown in FIG. 1. In this case the human and/or apparatus acts as an alternative to measurements taken by sensor electrodes 233. Electrode 233 is equipped with a series of holes to permit visibility of the test strip.

Finally, not shown in the figure is a temperature sensor, which may assist with calibration and measurement sensitivity, accuracy, and reliability.

Figure 3:
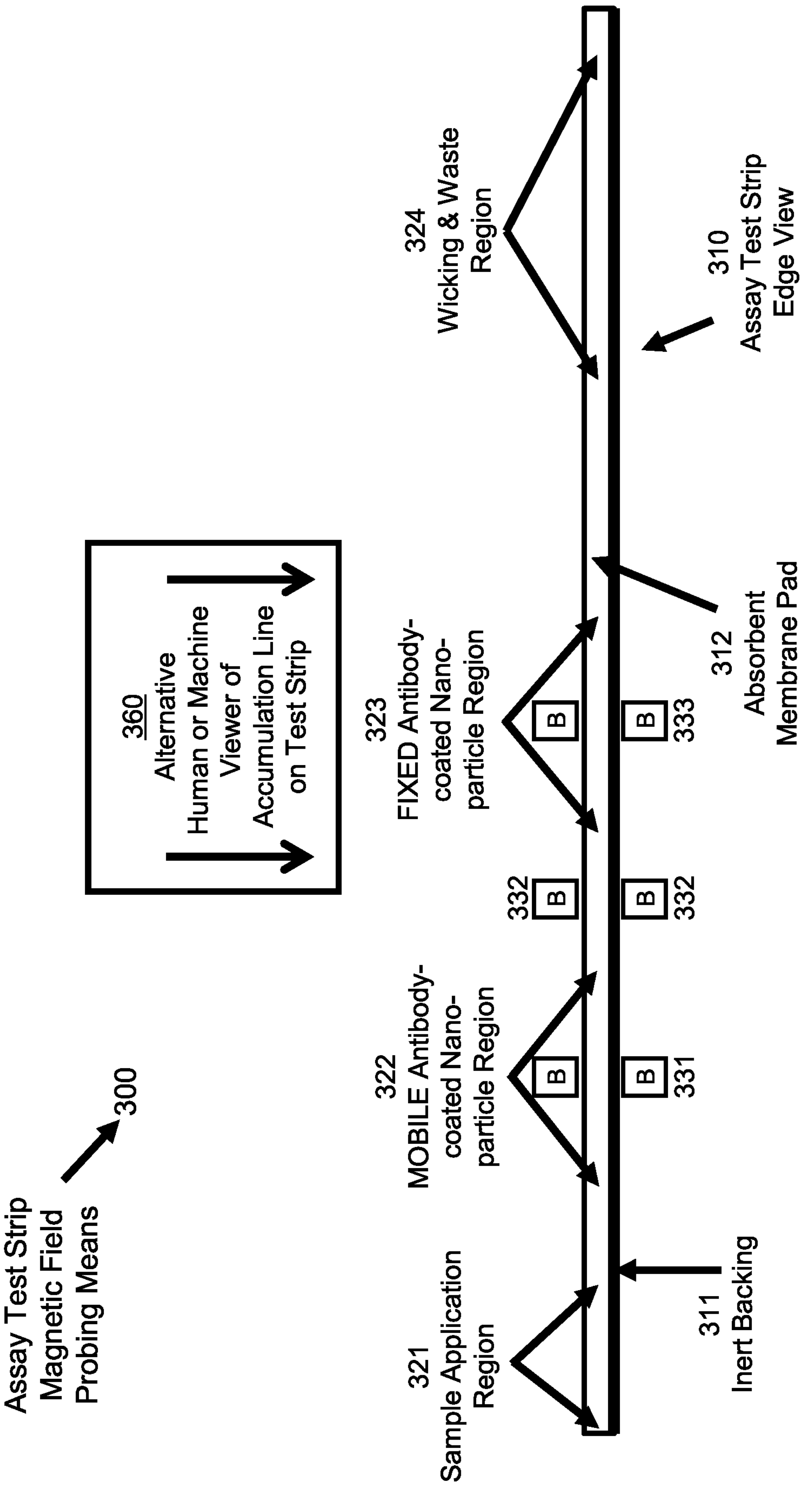
FIG. 3 shows a diagram that is identical to that of FIG. 2, except that the magnetic field 331, 332, 333 instead of electric field sensors are used.

FIG. 3 shows a diagram that is identical to that of FIG. 2, except that the magnetic field 331, 332, 333 instead of electric field sensors are used. Such sensors are used detect and/or quantify the presence of nanoparticles for which there are magnetic properties of any kind. For example, said sensors could quantify the average permeability of the region in their immediate vicinity.

FIGS. 2 and 3 show basic examples of the method taught in the instant disclosure. It should be understood that, depending upon the application, the test strip could include only the electric and/or magnetic sensors shown. It could also be outfitted with a temperature sensor, electronic or otherwise. It could contain excitation and/or signal conditioning circuitry for the sensors and wired or wireless means to operate with readout equipment. It could contain these adjuncts in various combinations.

Figure 4:
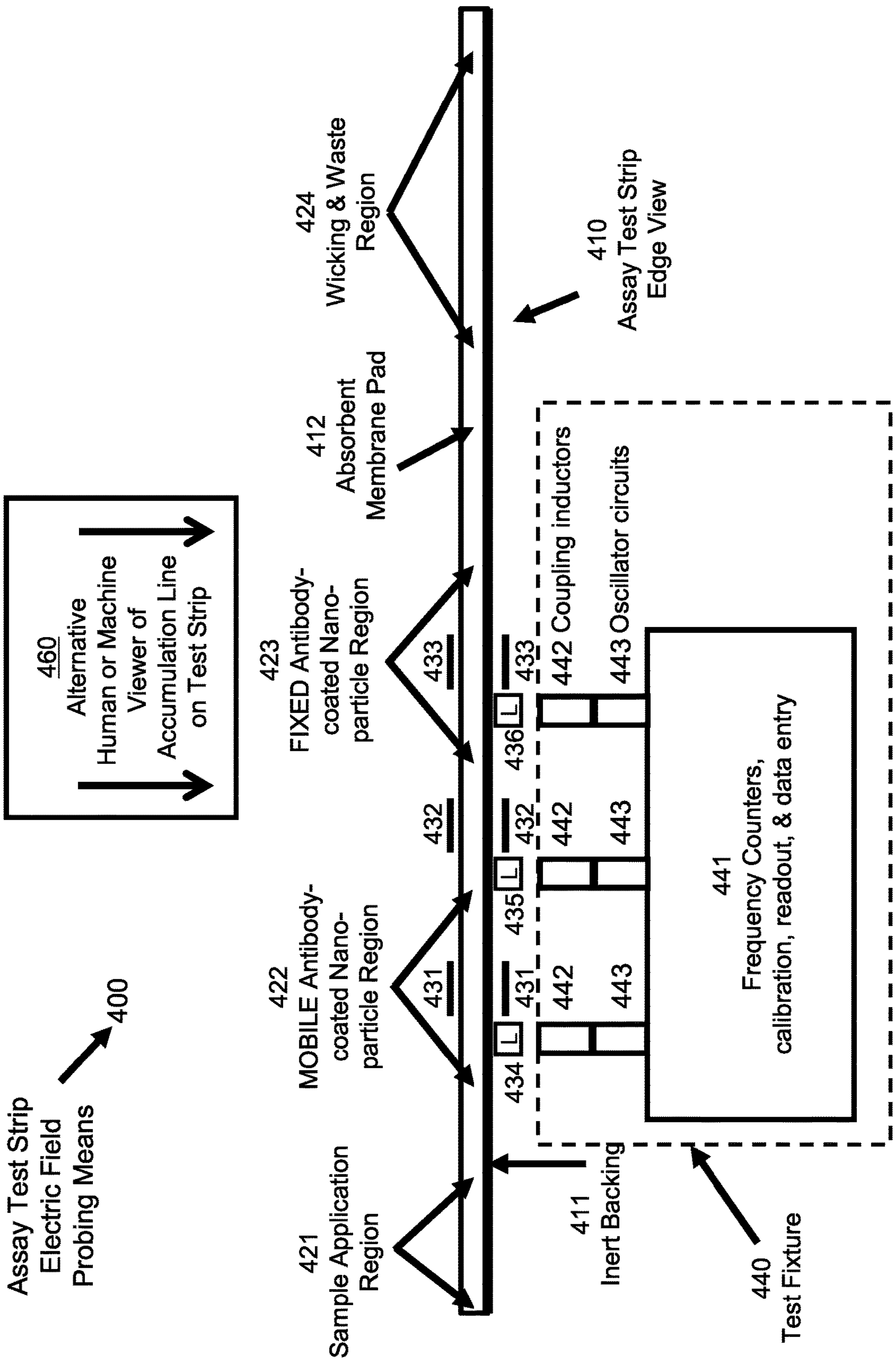
FIG. 4 illustrates the same electric field sensors—431, 432, 433—as in FIG. 2, each a capacitor plate at the top and bottom of test strip 410.

FIG. 4 illustrates the same electric field sensors—431, 432, 433—as in FIG. 2, each a capacitor plate at the top and bottom of test strip 410. In this case, there also exists a resonating inductor 434, 435, 436 connected across each sensor (wiring not shown) to form a resonant circuit, "sensor tuned circuit". Inductors 434, 435, 436 could for instances be attached to the bottom of the strip, printed on inert backing 411, or embedded in membrane pad 412, next to one edge of the strip so as not to affect wicked flow of the liquid sample.

Test fixture 441 contains all the remaining circuitry to affect the primary measurement. For instance, near each of the resonating inductors 434, 435, 436 could be a coupling inductor 442 that couples it to the remainder of an oscillator circuit 443; such that the tuned circuit on the test strip determines the frequency of this oscillator. As the average dielectric constant at a given sensor increases, from increased presence of antibody nano-particles, the frequency of oscillation decreases. Block 441 contains frequency counter(s) and all other circuitry needed for the measurements.

Figure 5:
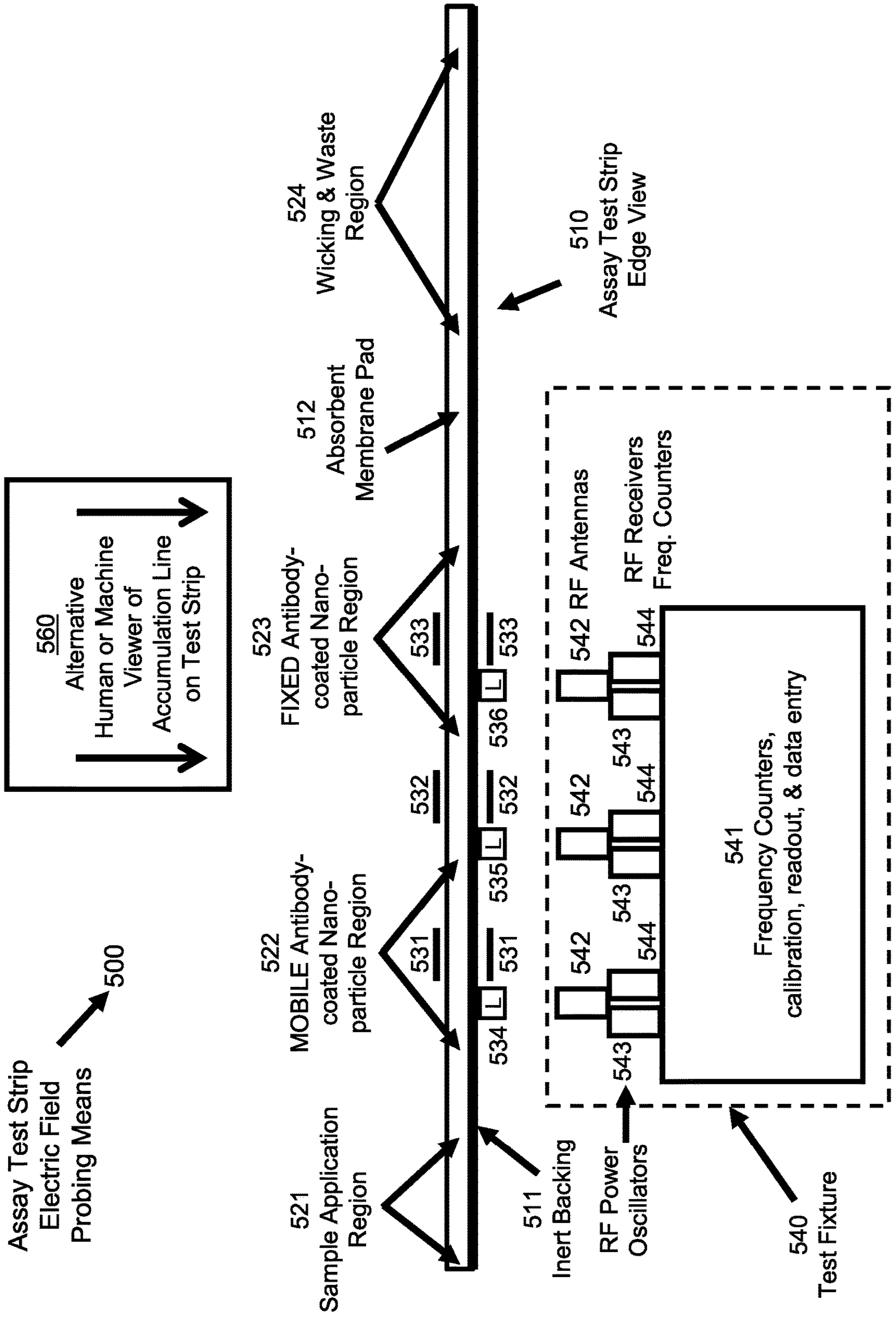
FIG. 5 describes a method to greatly mitigate oscillator frequency variations resulting from uncontrolled tolerances of the distance between a resonating inductor on the strip and the coupling inductor on the test fixture, and stray capacitance therefrom.

The embodiment depicted in FIG. 5 describes a method to greatly mitigate oscillator frequency variations resulting from uncontrolled tolerances of the distance between a resonating inductor on the strip and the coupling inductor 442 on the test fixture, and stray capacitance therefrom.

Relatively well separated from the Sensor Tuned Circuit on the test strip is an antenna 542 that is first fed by power oscillator source 543 operating at a frequency in the vicinity of the sensor tuned circuit's resonant frequency. As described for FIG. 4, the Sensor Tuned Circuit" consists of for instance sensor 531 and inductor 534. This antenna 542 radiates some of its energy into the sensor tuned circuit. The power oscillator's frequency is then swept, such that it passes the sensor tuned circuit's resonant frequency, at which frequency, some aspect of the RF power oscillator 543, such as power supply current flow, will indicate that maximum power is being absorbed into the sensor tuned circuit.

Resonant frequencies of each sensor could be measured at the factory and indicated on the sensor package or written into an RF ID strip. The factory readings could be compared with the readings after the sample has been applied.

In order to obtain a more accurate sensor resonant circuit frequency measurement, when the power oscillator's circuitry shows maximum absorption from the sensor tuned circuit, the oscillator could be switched off. The antenna 542 would then be switched to a sensitive receiver 544, which has been monitoring and recording the power oscillator's frequency. As soon as the power oscillator is shut off, the sensor tuned circuit will continue to oscillate on its own ("ring") for a period of time depending upon its Q factor. This oscillation is precisely at its own resonant frequency, which is captured by the sensitive receiver 544 and measured by a frequency counter.

Figure 6:
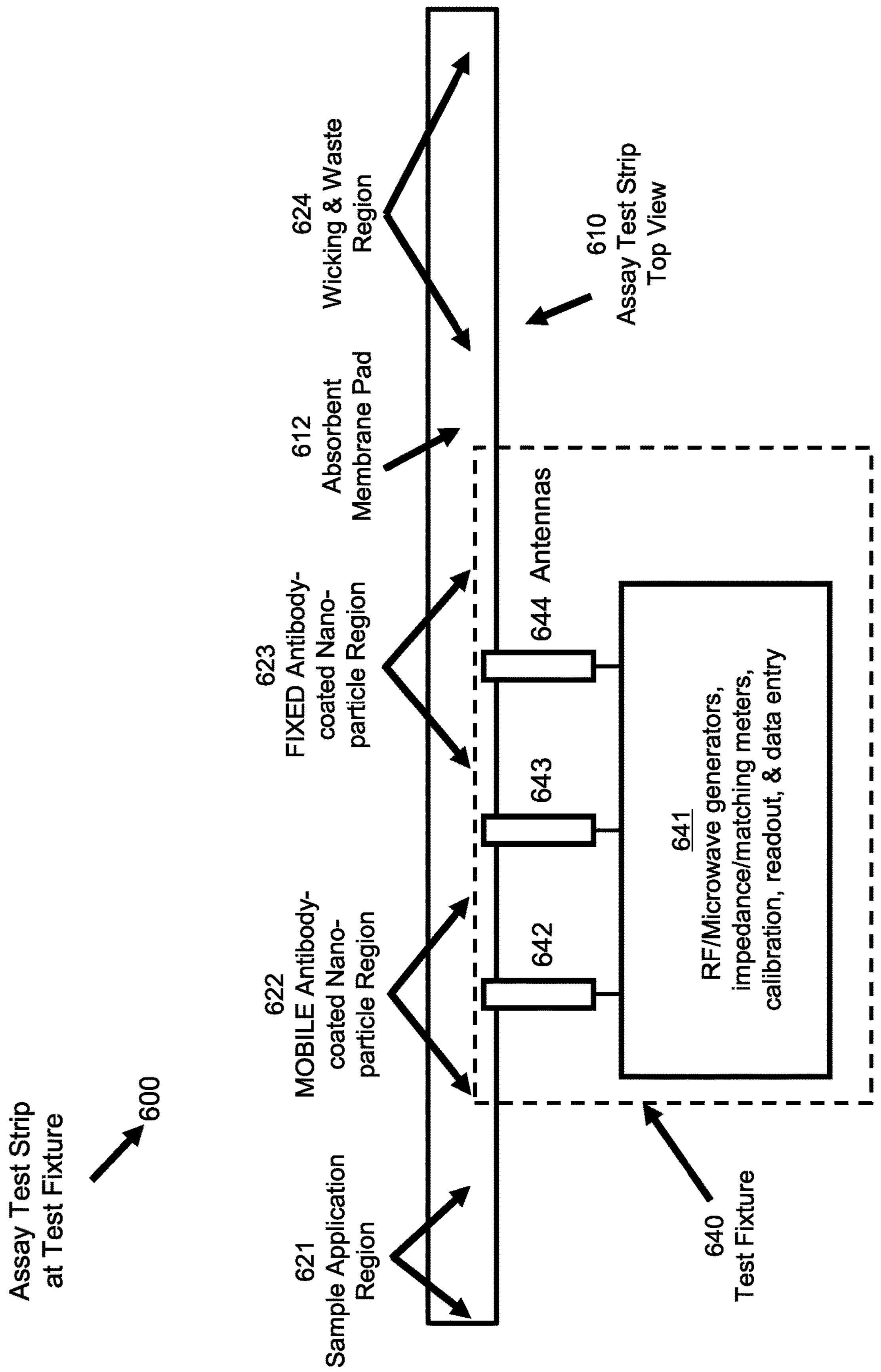
FIG. 6 shows a top view of the strip in FIG. 1, along with a set of antennas driven by RF impedance meters.

FIG. 6 shows a drawing of the same lateral flow assay test strip as FIG. 1, including that there are no sensors built into the strip. In FIG. 6, a top view of the strip, instead of a side view, is shown; so inert backing 111 is not visible. Unlike the previous two embodiments, this one requires no additions to the test strip, such as sensors, a considerably lower cost alternative.

Test Fixture 640 consists of a set of antennas 642, 643, 644 one each for several regions of the strip—622, 623, and the intermediate region near antenna 643. Each antenna is driven by an RF impedance meter and auxiliary circuitry 641. The presence and quantity of nanoparticles cause the antenna feed impedance to vary. The antenna 643 helps to distinguish between impedance changes due to fluid as opposed to nanoparticles; as when the process is complete, there is only fluid in membrane pad 612 at the region of antenna 643.

The exact antenna design, including directivity, as well as the frequency (wavelength) used for the RF/microwave generator-impedance meter are chosen such that antenna 642, 643, or 644 feed impedance is affected by test strip properties only or primarily within its region. For instance, a region, such as fixed antibody-coated particle region 623 may occupy 10 mm along test strip 610. Vehicular radar equipment operates at close to 79 GHz, wavelength about 4 mm. The technology for generating and radiating these frequencies, including with directivity and all contained on printed circuit boards is now well developed and has low cost.

Test Fixture 640 allows the user to obtain data from test strip 610, either continuously as the sample fluid is wicking through said strip, or at any time after the wicking process is complete.

For some applications, it may be helpful or even necessary to apply test strip 610 to the test fixture 640 to read the antenna impedance values as a baseline calibration, prior to applying the sample.

For some applications, it may be helpful or even necessary, including as part of the Quality Assurance procedure, to use an identical test fixture as 640 in the factory to read the antenna impedance values for each test strip or batch thereof, as a baseline calibration. These readings could be furnished with each test strip, including as a code designation, which could be entered by the user when reading the used test strip or strips.

Figure 7:
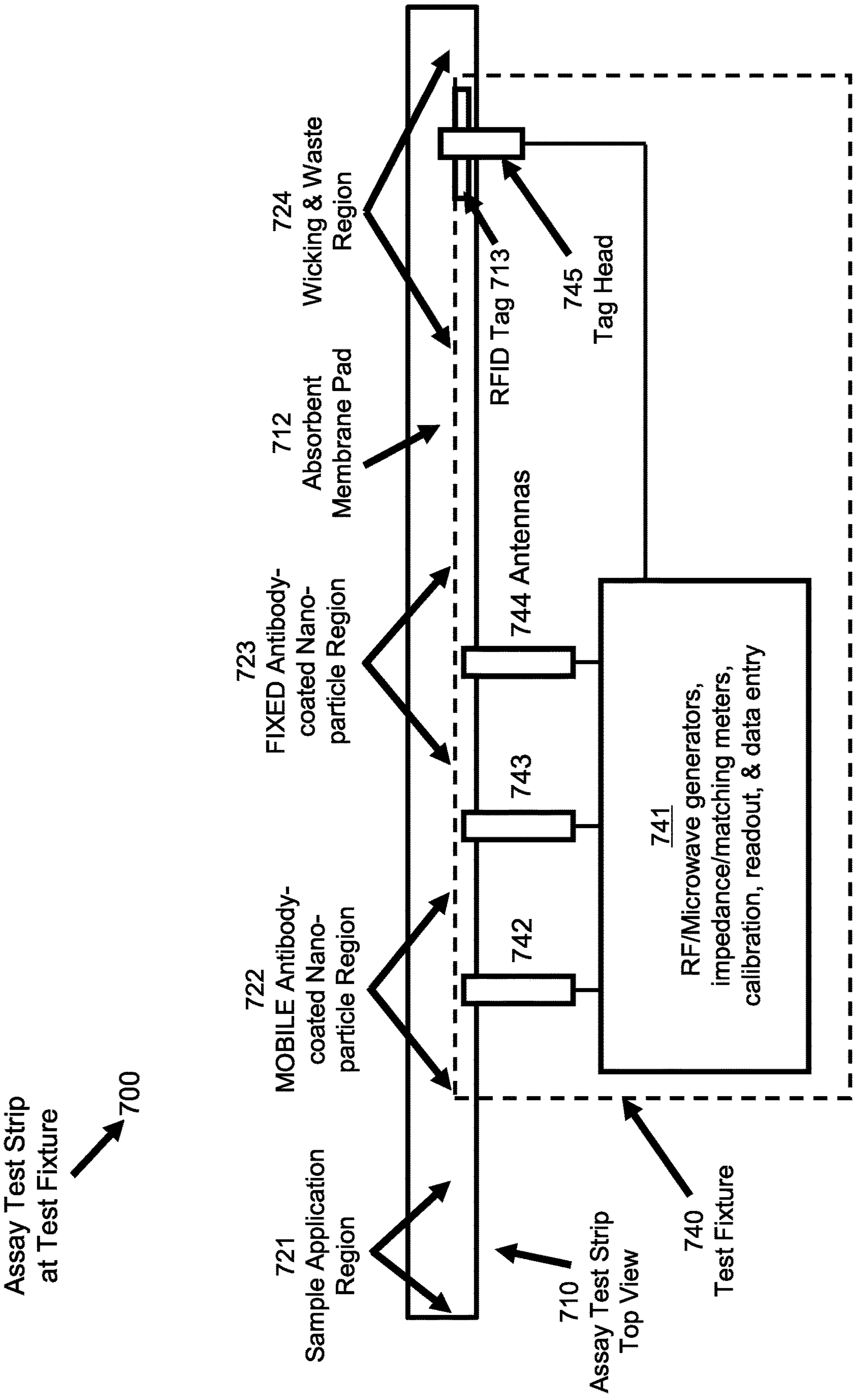
FIG. 7 adds a passive RFID tag to FIG. 6.

FIG. 7 is identical to FIG. 6, except that a passive tag is included with assay test strip 713, and a tag head 745 is included with test fixture 740. If baseline calibration readings are made at the factory, the results can be stored on RFID tag 713. This information could be read in conjunction with tag head 745 and used to calibrate the data from the sample, assuming this is needed.

Figure 8:
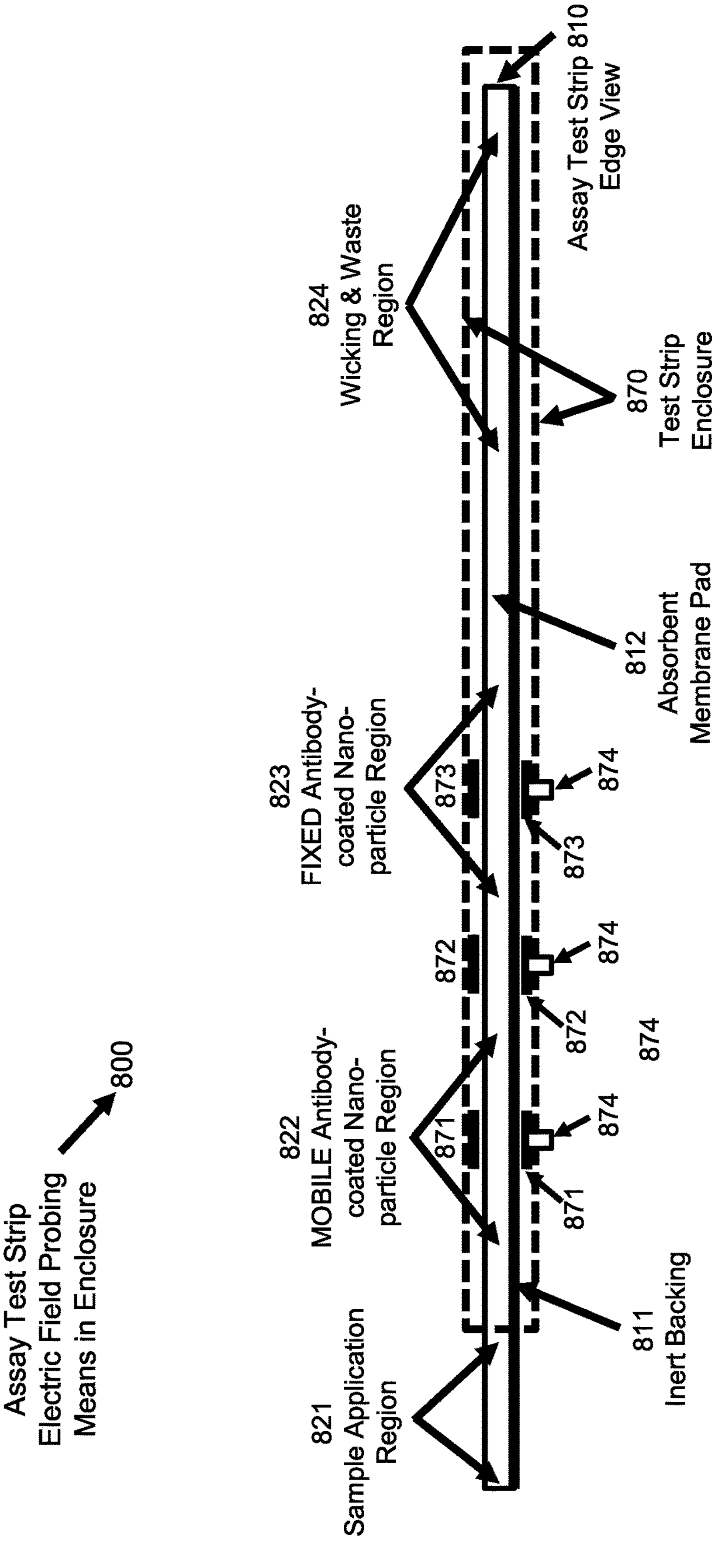
FIG. 8 illustrates the concept of attaching sensors to a test strip enclosure, instead of to the assay test strip itself.

FIG. 8 illustrates the concept of attaching sensors to the test strip enclosure 870, instead of to the assay test strip 810 itself. The sensors shown for this example 871, 872, 873 are the electric field type, but this concept applies to many different types of sensors. Assay test strip enclosures are mass manufactured to precision dimensional standards, which supports the practicality of attaching sensors to them and maintaining the correct physical relationship with regions of the test strip. Moreover, no modifications whatsoever are needed for assay test strip 810.

The sensors could be attached to circuit boards, which are in turn attached to the enclosures. Any additional circuitry, not shown, could be included with the sensors on the circuit board to facilitate their operation, calibration, and record keeping.

FIG. 8 also illustrates the concept of wired instead of wireless methods to couple with the sensors. Contacts 874, shown for only the lower planar electrodes, can be attached directly to each sensor electrode or through the intermediary of a circuit board.

The test fixture, not shown, can be fitted with contacts mating with those protruding from the test strip enclosure. For the particular example shown in FIG. 8, the test fixture contains all of the circuitry to measure the average dielectric constant between each set of electrodes that comprise each sensor. Each sensor appears in an electric circuit as a capacitance, the value of which can be measured by numerous types of circuits, such as for instance the frequency of an oscillator.

The details provided in the above description describe particular implementations of the systems for performing the measurements described. Other embodiments could be implemented in any other suitable manner. For example, particular voltages, frequencies, noise levels, gains, resistances, capacitances, and other values may be described. These values are for illustration only. It may be advantageous to set forth definitions of certain words and phrases used throughout this patent document. The term "couple" and its derivatives refer to any direct or indirect communication between two or more elements, whether or not those elements are in physical contact with one another. The terms "transmit," "receive," and "communicate," as well as derivatives thereof, encompass both direct and indirect communication. The terms "include" and "comprise," as well as derivatives thereof, mean inclusion without limitation. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

Many different arrangements of the various components depicted, as well as components not shown, are possible without departing from the spirit and scope of the present disclosure. Embodiments of the present disclosure have been described with the intent to be illustrative rather than restrictive. Alternative embodiments will become apparent to those skilled in the art that do not depart from its scope. A skilled artisan may develop alternative means of implementing the aforementioned improvements without departing from the scope of the present disclosure.

It will be understood that certain features and subcombinations are of utility and may be employed without reference to other features and subcombinations and are contemplated within the scope of the claims. Not all steps listed in the various figures need be carried out in the specific order described.

The disclosure claimed is:

1. A method for reading a lateral flow assay test strip, comprising:

providing a microwave antenna in immediate proximity of a stain line region of said test strip;

causing a chemical compound to travel to said stain line region, an amount of said chemical compound varying in accordance with a quantity of an analyte;

connecting an instrumentation to said microwave antenna, said instrumentation including a radio frequency meter;

measuring a feed impedance of said microwave antenna using said instrumentation, said feed impedance of said microwave antenna varying with said amount of said chemical compound; and using said variation in said feed impedance of said microwave antenna to determine said quantity of said analyte.

2. The method of claim 1, further comprising providing said microwave antenna and said instrumentation on a test fixture.

3. The method of claim 2, wherein said lateral flow assay test strip is devoid of any electronic device.

4. The method of claim 1, further comprising providing another microwave antenna immediately proximate another stain line region of said test strip.

5. The method of claim 2, wherein said microwave antenna comprises a plurality of said microwave antennas and said instrumentation comprises a plurality of instrumentations.

6. The method of claim 5, wherein said plurality of microwave antennas and said plurality of instrumentations are provided on said text fixture as sets, each said set comprising at least one of said plurality of microwave antennas and at least one of said plurality of instrumentations, a first set being associated with said stain line region, a second being set associated with a mobile antibody-coated nano-particle region of said test strip, and a third set located between said stain line region and said mobile antibody-coated nano-particle region.

7. The method of claim 6, wherein said feed impedance of each said set is measurable: (a) before a lateral flow sample is inserted; (b) while said lateral flow sample is propagating through said test strip; and (c) after said lateral flow sample propagation is completed.

8. A method for reading a lateral flow assay test strip, comprising:

providing a microwave antenna in proximity of a stain line region of said test strip;

causing a chemical compound to travel to said stain line region, an amount of said chemical compound varying in accordance with a quantity of an analyte;

connecting an instrumentation to said microwave antenna;

measuring a feed impedance of said microwave antenna using said instrumentation, said feed impedance of said microwave antenna varying with said amount of said chemical compound; and determining said quantity of said analyte based on said feed impedance of said microwave antenna.

9. The method of claim 8, further comprising situating said test strip within a test fixture for said determination of said quantity of said analyte.

10. The method of claim 9, further comprising providing said microwave antenna and said instrumentation within said test strip.

11. A method for reading a lateral flow assay test strip, comprising:

providing a microwave antenna in proximity of a stain line region of said test strip;

causing a chemical compound to travel to said stain line region, an amount of said chemical compound varying in accordance with a quantity of an analyte;

connecting an instrumentation to said microwave antenna;

measuring a feed impedance of said microwave antenna using said instrumentation, said feed impedance of said microwave antenna varying with said amount of said chemical compound; and determining said quantity of said analyte based on said feed impedance of said microwave antenna using a test fixture.

* * * * *